United States Patent [19]
Shigemori et al.

[11] Patent Number: 6,132,972
[45] Date of Patent: Oct. 17, 2000

[54] METHOD FOR DETECTING NUCLEIC ACIDS THROUGH A TRIPLE-STRANDED DNA INTERMEDIATE WITHOUT DENATURING

[75] Inventors: Yasushi Shigemori; Jun Fujiwara, both of Kisarazu, Japan

[73] Assignee: Aisin Cosmos R & D Co., Ltd., Japan

[21] Appl. No.: 09/196,643

[22] Filed: Nov. 19, 1998

[30] Foreign Application Priority Data

Nov. 19, 1997 [JP] Japan .................................. 9-333735

[51] Int. Cl.[7] .............................. C12Q 1/68; C12Q 1/44; C12Q 1/37
[52] U.S. Cl. .................................. 435/6; 435/19; 435/23
[58] Field of Search .................................. 435/6, 19, 23

[56] References Cited

U.S. PATENT DOCUMENTS

| | | | |
|---|---|---|---|
| 5,460,941 | 10/1995 | Camerini-Otero et al. | 435/6 |
| 5,707,811 | 1/1998 | Ferrin et al. | 435/6 |
| 5,750,338 | 5/1998 | Collins et al. | 435/6 |

FOREIGN PATENT DOCUMENTS 9-220099   8/1997   Japan .

OTHER PUBLICATIONS

Cheng, Suzanne et al., "Use of Psoralen–modified Oligonucleotides to Trap Three–stranded RecA–DNA Complexes and Repair of These Cross–linked Complexes by ABC Excinuclease"; *The Journal of Biological Chemistry*; 263(29):15110–15117; 1988.

*Primary Examiner*—Carla J. Myers
*Assistant Examiner*—Diana Johannsen
*Attorney, Agent, or Firm*—Christensen O'Connor Johnson & Kindness, PLLC

[57] ABSTRACT

A nucleic acid detecting method using a probe is provided which makes it possible to obtain correct information on a target double-stranded DNA dsDNA without damaging the target double-stranded DNA dsDNA. In the nucleic acid detecting method of the present invention, a nucleic acid is detected by subjecting the target double-stranded DNA dsDNA bound with a first single-stranded DNA dsDNA probe via recA protein to a treatment with a single-stranded DNA dsDNA specific nuclease, to thereby allow a second single-stranded DNA dsDNA probe consisting of a base sequence complementary to that of the first probe or a part thereof and labeled with a detectable marker to bind to the target DNA dsDNA.

2 Claims, 2 Drawing Sheets

SEQUENCE LISTING

<160> NUMBER OF SEQ ID NOS: 3

<210> SEQ ID NO 1
<211> LENGTH: 120
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: misc. feature
<222> LOCATION: (1)...(120)
<223> OTHER INFORMATION: oligonucleotide probe

<400> SEQUENCE: 1
gaccgtctcc gggagctgca tgtgtcagag gttttcaccg tcatcaccga aacgcgcgag      60
gcagctgcgc taaagctcat cagcgtcctc gtgaagcgat tcacagatgt ctgcctgttc    120

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: misc. feature
<222> LOCATION: (1)...(35)
<223> OTHER INFORMATION: oligonucleotide probe

<400> SEQUENCE: 2
gatgagcttt accgcagctg cctcgcgcgt ttcgg                                35

<210> SEQ ID NO 3
<211> LENGTH: 120
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: misc. feature
<222> LOCATION: (1)...(120)
<223> OTHER INFORMATION: nonspecific oligonucleotide probe

<400> SEQUENCE: 3
aggcatcgtg gtgtcacgct cgtcgtttgg tatggcttca ttcagctccg gttcccaacg     60
atcaaggcga gttacatgat cccccatgtt gtgcaaaaaa gcggttagct ccttcggtcc    120

METHOD FOR DETECTING NUCLEIC ACIDS THROUGH A TRIPLE-STRANDED DNA INTERMEDIATE WITHOUT DENATURING

FIELD OF THE INVENTION

The present invention relates to a method for detecting a target double-stranded DNA through a triple-stranded DNA intermediate without denaturing process.

BACKGROUND OF THE INVENTION

The present invention relates to a method for detecting a double-stranded DNA having a defined nucleotide sequence by using a single-stranded probe.

Screening a DNA having a defined sequence is a technique for use in molecular biology and in the clinical test field. In particular, it is a basic technique for use in gene cloning and detecting genetic disorders. As a conventional DNA detection method, a Southern blot technique is widely used which detects a single-stranded DNA (hereinafter ssDNA) having a defined nucleotide sequence by binding a labeled probe to the ssDNA sample which has been prepared by denaturing treatment. On the other hand, as a method enabling direct detection of the double-stranded DNA (hereinafter dsDNA) having a defined sequence in a dsDNA sample without the denaturing treatment, the following techniques are known in the prior art.

A first method is characterized in that an oligonucleotide probe is allowed to bind to a target DNA having a defined nucleotide sequence via recA protein to form a complex consisting of these three substances (hereinafter, referred to as "recA recombinant intermediate")(Cheng et al., J. Biol. Chem, 263, 15110–15117, 1988). In this method, after a recA protein digestion reaction, which is required for subjecting the dsDNA sample to a separation gel, a photocrosslinking reaction is performed to prevent the binding of the oligonucleotide probe to the target dsDNA from being unstable. In this manner, stable binding between the target dsDNA and the probe is attained. The ultraviolet irradiation during the photocrosslinking reaction has drawbacks not only in producing a non-specific binding of the probe to the target DNA but also in damaging the target DNA itself.

To overcome the problems in the prior art, the present inventors have disclosed a method for detecting a specific nucleotide sequence in the double-stranded nucleic acid without causing damage to nucleic acids, in Japanese Patent Publication No. 8-54278. In the second method mentioned above, instead of binding the probe to the target dsDNA by the photocrosslinking reaction, a probe is fixed onto the target DNA in the form of loop under mild conditions using enzyme reactions. Thus, this method is free from the drawback of damaging the target dsDNA. However, in this method, a probe-bound DNA finally produced does not fully represent the size and shape of the target dsDNA molecule correctly in the detection step with the separation gel.

BRIEF SUMMARY OF THE INVENTION

The present invention is made with the view toward overcoming the drawbacks of the aforementioned invention made by the present inventors. An object of the present invention is to provide a method for detecting a target dsDNA, which enables to obtain correct information on the target dsDNA, including a size and a shape of the DNA molecules and which does not damage the dsDNA.

To solve the aforementioned problems and to thereby attain the object, the nucleic acid detection method according to the present invention is constituted as follows.

The present invention is a method for detecting a double-stranded DNA with a defined nucleotide sequence from a double-stranded DNA sample, by using a single-stranded DNA probe with the defined nucleotide sequence, which is characterized by comprising the steps of:

(1) mixing recA protein, a first single-stranded DNA probe and the double-stranded DNA with the defined nucleotide sequence, thereby forming a first complex of the double-stranded DNA bounded with the first single-stranded DNA probe via recA protein;

(2) digesting the first complex by allowing a single-stranded DNA specific nuclease to act upon the first complex;

(3) digesting recA protein by allowing a proteolytic enzyme to act upon a digestion product obtained in the step (2), to dissociate the single-stranded DNA probe from the digestion product;

(4) adding a second single-stranded DNA probe which consists of a nucleotide sequence complementary to the defined nucleotide sequence or a part thereof and which is labeled with a detectable marker, to the dissociation product obtained in the step (3), to form a second complex consisting of these two components mentioned above; and (5) detecting the marker incorporated in the second complex.

DETAILED DESCRIPTION OF THE INVENTION recA protein used in the present invention is originally a protein responsible for a recombination reaction involved in a kind of DNA repair reaction, by which a mutation site resulting from mutation to a DNA, is replaced with a normal nucleotide sequence. In the present invention, recA protein is used for forming the recA recombinant intermediate by permitting the first ssDNA probe to specifically bind to the defined nucleotide sequence of the target dsDNA.

The first ssDNA probe used herein is a DNA containing a part of the defined nucleotide sequence of the dsDNA to be detected, and preferably a DNA having 10–150 nucleotide.

As the dsDNA sample, any DNA sample including a genomic DNA sample may be used.

Then, ssDNA specific nuclease is allowed to act on the recA recombinant intermediate to digest it. ssDNA specific nuclease used herein is an enzyme which specifically digests only the ssDNA. The digestion reaction with the ssDNA specific nuclease is a first feature of the present invention. Any ssDNA specific nuclease may be used in the present invention. As a preferable ssDNA specific nuclease, nuclease S1 is mentioned.

After the digestion reaction with the ssDNA specific nuclease, a proteolytic reaction is performed in order to dissociate the ssDNA probe from a digestion product. It follows that recA protein is digested and the first ssDNA probe binding to the digestion product via recA protein, is dissociated from the digestion product. The step is intended to contribute to eliminating a non-specific binding completely from the probe.

Subsequently, binding operation is performed for permitting the second ssDNA probe to bind to the dissociation product obtained. The second ssDNA probe is a DNA with a nucleotide sequence complementary to that of the first ssDNA probe or a part thereof. Note that the target dsDNA cannot be detected, if a DNA consisting of the same nucleotide sequence as that of the first probe or a part thereof is used as the second single-stranded probe. Preferably, the second ssDNA probe should have 5 to 150 bases.

Since the second ssDNA probe is labeled with a detectable marker, it is possible to detect the dsDNA containing the defined nucleotide sequence from the dsDNA sample.

The preferable marker may be, but not limited to a radioisotope, fluorescent substance, biotin, and digoxigenin.

Furthermore, since the second ssDNA DNA probe is bound to the target DNA under mild conditions, the digested DNA is free from damages.

Figure 1:
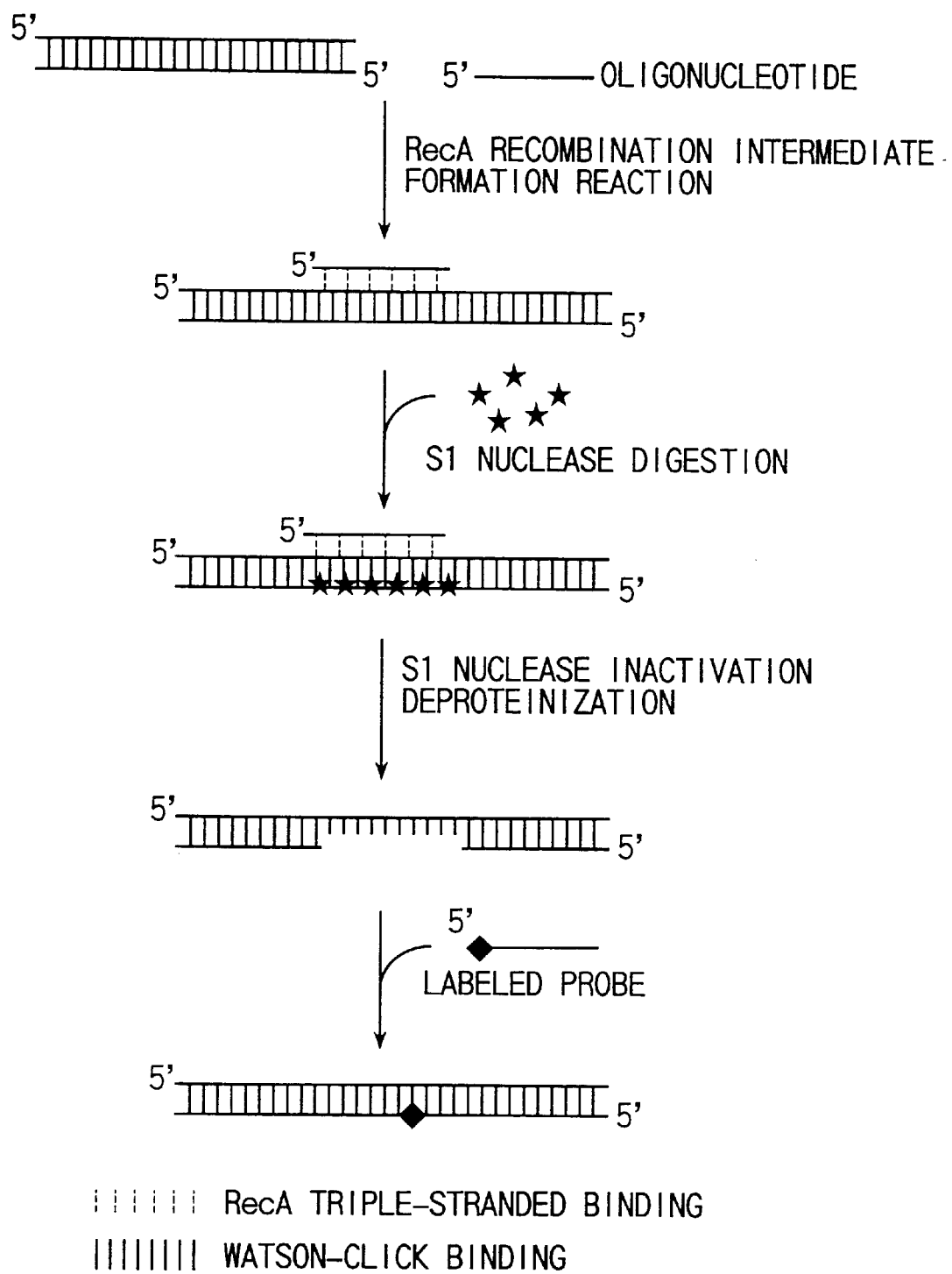
FIG. 1 is a view schematically showing a putative process of the DNA detection method of the present invention.

It is apparent, from the results of Examples described later, that the dsDNA having the defined nucleotide sequence can be detected by the method of the present invention. Although it is not intended to constrain to any theory, to facilitate understanding of the present invention, a putative process thereof will be explained as follows:

Hereinbelow, the putative process will be explained with reference to FIG. 1.

In a first stage of the reaction, a recA protein intermediate forming reaction is performed to form the recA protein intermediate by mixing the dsDNA sample, the first ssDNA probe and recA protein. In the recA recombinant intermediate, the first ssDNA probe is bound to a specific site of the nucleotide sequence of the dsDNA (site having the same sequence as that of the first probe) via recA protein in an unknown binding manner indicated by a doted line in the figure. The reaction is well known.

In a second stage of the reaction, a nuclease S1 digestion reaction is performed in which nuclease S1 is allowed to act on the recA recombinant intermediate. In consideration that this reaction enables the following reaction for binding the second probe to the target DNA, it is strongly suggested that the target DNA is digested with nuclease S1.

In a third stage of the reaction, recA protein is digested with a proteolytic enzyme. recA protein is digested during this reaction, with the result that the first ssDNA is dissociated from the target DNA. This reaction is well known.

In a fourth stage of the reaction, the second ssDNA probe is hybridized to the target DNA which has been subjected to the digestion reaction. The digested site is suggested to be a nucleotide sequence in the target DNA that is complementary to the defined nucleotide sequence to which the first ssDNA is bound, since the second ssDNA probe with the same nucleotide sequence as that of the first ssDNA probe or a part thereof does not bind to the target DNA, but the one with the complementary sequence to that of the first ssDNA probe or a part thereof does bind.

Modified Example

A site specific mutation can be introduced by using a ssDNA with the nucleotide sequence complementary to the defined sequence except that one or several nucleotide(s) is (are) replaced with a desired nucleotide(s), as the second ssDNA probe.

Since the present invention makes it possible to label any dsDNA containing the defined nucleotide sequence, with a marker substance, the present invention may be used as a method for isolating a specific DNA from a genomic DNA sample or a restriction enzyme fragment. The present invention is therefore useful for genetic treatment or gene cloning.

In the nucleic acid detection method mentioned above, the nucleotide labeled with a detectable marker and DNA polymerase could be used to directly incorporate the labeled nucleotide into the dissociation product, in place of the ssDNA probe binding step. In this way, it is possible to detect the target DNA. According to this method, detection can be made with a higher sensitivity.

EXAMPLES

Example 1

Dependency on recA Protein and Nuclease S1 and Specificity of a First ssDNA Probe in the DNA Detection Method According to the Present Invention To prove that recA protein and nuclease S1 are essential components in the DNA detection method of the present invention, and that the dsDNA containing the nucleotide sequence of the first ssDNA probe is specifically detected, the following experiments were performed.

Standard conditions are employed as experimental conditions as shown below. All components are added which are considered essential for the nucleic acid detection method according to the present invention.

Experimental Materials and Method

1. Formation of the recA Recombinant Intermediate to form the recA recombinant intermediate, reaction solution A and reaction solution B were prepared as follows.

| Reaction solution A: | |
|---|---|
| Oligonucleotide probe (SEQ ID NO:1) | 5 pmol |
| recA protein | 3.0 µg |
| ATP-γS | 0.48 mM |
| Reaction solution B: | |
| Target straight-chain DNA | 200 ng |
| ATP-γS | 0.48 mM |

The oligonucleotide probe in the reaction solution A was a ssDNA having 120 nucleotides (SEQ ID NO:1). recA protein was available from Epi Center Technology Co., Ltd. The concentration of ATP-γS (Boehringer Mannheim CO., Ltd.) was a final concentration. As the buffer, 30 mM Tris acetate (pH 7.2)+2.5 mM magnesium acetate buffer was used.

The target straight-chain DNA in the reaction solution B was a plasmid pBR322DNA which was linearized with restriction enzyme Nde I. The plasmid pBR322DNA is a known DNA which shares the nucleotide sequence of the oligonucleotide probe (SEQ ID NO:1). As the buffer, 30 mM Tris acetate (pH 7.2)+2.15 mM magnesium acetate buffer was used.

After the reaction solution A and the reaction solution B were incubated at 37° C. for 15 minutes, independently, both reaction solutions were mixed and further incubated at 37° C. for 30 minutes. The volume of the combined solution was 20 μL.

2. Digestion Reaction with Nuclease S1

Subsequently, the whole solution was added to an enzyme reaction solution containing the ssDNA specific nuclease to make a total of a 100 μL solution. The resultant mixture was heated at 45° C. for 100 minutes. In this experiment, nuclease S1 (Takara Shuzo Co., Ltd.) was used as the ssDNA specific nuclease.

The enzyme reaction solution was constituted as follows:

| Nuclease S1 | 200 units |
|---|---|
| Sodium acetate (pH 4.6) | 30 mM |
| NaCl | 280 mM |
| ZnSO$_4$ | 1 mM |

To terminate the reaction, 150 mM Tris-HCl (pH 8.8) and 20 mM EDTA were added. The resultant mixture was incubated at 45° C. for 30 minutes to inactivate nuclease S1.

3. Binding of the Second Probe to the Target DNA

To the total volume of the reaction solution, 1/10 vol. of 3M sodium acetate and 2-vols. of ethanol were added. The resultant mixture was cooled and centrifuged to isolate and concentrate DNA molecules. After the DNA precipitate thus obtained was dissolved in 10 μL of distilled water, a deproteinization reaction solution (10 mM EDTA, 0.5% (W/V) SDS, 0.7 mg/mL proteinase K (final concentration)) was added. To the resultant mixture, 2.5 pmol of the second oligonucleotide probe (SEQ ID NO:2) having 35 nucleotides and labeled with digoxigenin at its 3' end, was added to give a mixture of 25 μL in total. The resultant mixture was heated at 55° C. for 15 minutes.

4. Electrophoresis and Detection for DNA

The whole of the mixture was applied to 0.8% agarose gel electrophoresis. After the electrophoresis, ethidium bromide staining was performed. The gel photograph was recorded and the gel was treated with 0.25N HCl with being immersed to depurinate the DNA in the gel. In this manner, the DNA in the gel were transferred onto a nylon membrane ("Biodyne A" manufactured by Japan Pall Ltd.) by the use of a capillary phenomenon and then fixed by ultraviolet rays. After the membrane was blocked (Boehringer Mannheim) at room temperature for 60 minutes, alkaline phosphatase coupled anti-digoxigenin antibody was allowed to react in the blocking solution at room temperature for 30 minutes. After the reaction, the resultant mixture was washed with a 150 mM Tris-HCL (pH 7.5) and 100 mM NaCl washing solution two times for 15 minutes each, and CDP-Star (Amersham Co., Ltd.) was added to the reaction mixture in an appropriate amount. After the resultant mixture was allowed to react at room temperature for 5 minutes, the membrane was brought into contact with instant film to detect a signal.

Result

Figure 2:
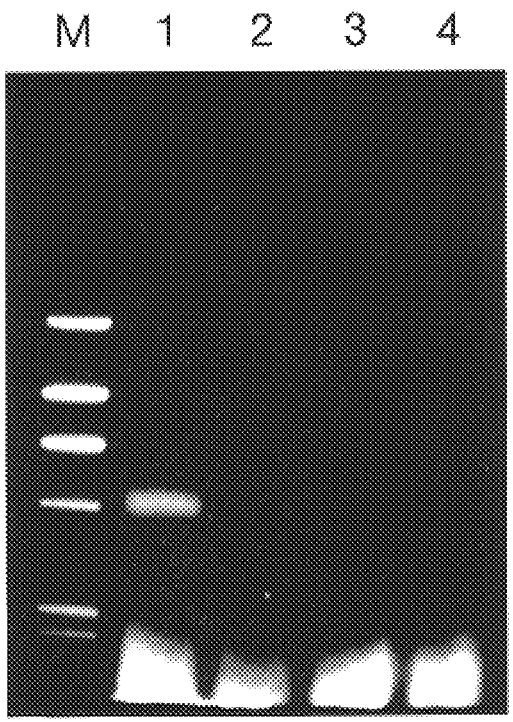
FIG. 2 is a photograph showing electrophoretic results obtained by a chemiluminescent detection method in an experiment for checking specificity of a first probe and dependency on recA protein and nuclease S1 according to the DNA detection method of the present invention.
Figure 3:
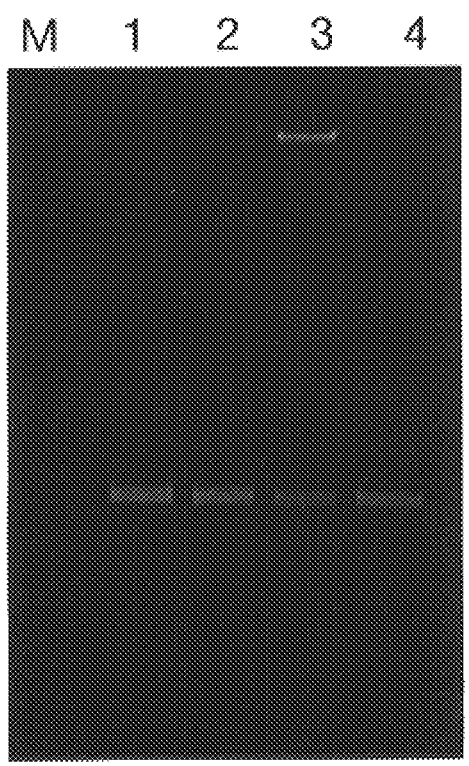
FIG. 3 is a photograph showing the elecrophoretic results obtained by a detection method using ethidium bromide staining in an experiment for checking specificity of a first probe and dependency on recA protein and nuclease S1 according to the DNA detection method of the present invention.

The results of the experiments described in the aforementioned examples are shown in FIGS. 2 and 3. The gel shown in FIG. 2 illustrates the results obtained by the chemiluminescent detection method (detection specific to DNA bound with the second probe). The gel shown in FIG. 3 illustrates the results of detection with ethidium bromide (non-specific detection to DNA).

Lane M represents a size marker (λ/Hind III DNA fragments).

Lane 1 is the results of the experiment conducted by adding all components required for the present invention. The signal is detected in both FIGS. 2 and 3. It is therefore demonstrated that the dsDNA having the defined nucleotide sequence can be detected by the method of the present invention.

Lane 2 shows the results of the experiment conducted with a nonspecific probe (SEQ ID NO:3) to the target DNA as the first probe. Although a band is detected in the gel of FIG. 3, no band is detected in the gel of FIG. 2. The present invention therefore proves that it is necessary to use the specific probe to the target DNA as the first prove in order to specifically detect the dsDNA.

Lane 3 and Lane 4 show the results of the experiments conducted without recA protein and nuclease S1, respectively. Bands are detected in both lanes in the case of the gel shown in FIG. 3; however, no bands are detected in the case of the gel of FIG. 2. It is therefore concluded that recA protein and nuclease S1 are essential for detecting the dsDNA specifically according to the present invention.

From the above results, recA protein, nuclease S1 and the first probe (SEQ ID NO:1) specific to the target DNA are all indispensable components for the detection method of a target dsDNA according to the present invention. It is demonstrated that specific detection of the defined target dsDNA is attained by the method of the present invention.

Effects of the Present Invention

In the reaction process of the nucleic acids detection method according to the present invention, it is possible to detect the dsDNA by bringing ssDNA probe into direct contact with dsDNA without performing the denaturation reaction required for the Southern blot method.

It is possible to obtain the target DNA having the same size and shape as an original DNA by using the DNA with a nucleotide sequence complementary to the defined nucleotide sequence as a second ssDNA probe, and thus to obtain correct information on the target DNA.

It is possible to attach a marker specifically to the target DNA with a defined nucleotide sequence. This technique can be applied to isolate a specific DNA from a DNA mixture such as genome and to isolate a specific DNA fragment from a restriction enzyme fragment mixture for gene cloning.

Since it is not necessary to irradiate intensive UV rays, the target nucleic acids are not damaged.

What is claimed is:

1. A method for detecting a double-stranded DNA in a sample, which method comprises the steps of:
   (a) adding a recA protein and a DNA probe comprising a target DNA sequence into a sample, the sample comprising a double-stranded DNA comprising a first strand comprising the target DNA sequence and a second strand comprising a DNA sequence complementary to the target DNA sequence, the recA protein, the double-stranded DNA and the DNA probe forming a complex wherein the DNA probe is bound to the double-stranded DNA by the recA protein;
   (b) digesting the DNA sequence complementary to the target DNA sequence with a single-stranded DNA specific nuclease, thereby yielding a partially-digested double-stranded DNA;
   (c) digesting the recA protein thereby dissociating from the complex the DNA probe and the partially-digested double-stranded DNA;
   (d) hybridizing an oligonucleotide probe labeled with a detectable marker to the partially-digested double-stranded DNA, the oligonucleotide probe comprising a sequence complementary to the target sequence or a portion thereof; and
   (e) detecting the detectable marker in the oligonucleotide probe hybridized to the partially-digested double-stranded DNA, thereby detecting the partially digested double-stranded DNA in the sample, wherein the presence of the partially digested double-stranded DNA is indicative of the presence of the double-stranded DNA in the sample.

2. A method for detecting a double-stranded DNA in a sample, which method comprises the steps of:
   (a) adding a recA protein and a DNA probe comprising a target DNA sequence into a sample, said sample comprising a double-stranded DNA comprising a first strand comprising the target DNA sequence and a second strand comprising a DNA sequence complementary to the target DNA sequence, the recA protein, the double-stranded DNA and the DNA probe forming a complex wherein the DNA probe is bound to the double-stranded DNA by the recA protein;
   (b) digesting the DNA sequence complementary to the target DNA sequence with a single-stranded DNA specific nuclease, thereby yielding a partially-digested double-stranded DNA;
   (c) digesting the recA protein thereby dissociating from the complex the DNA probe and the partially-digested double-stranded DNA;
   (d) utilizing DNA polymerase to incorporate labeled nucleotides into the partially-digested double-stranded DNA; and
   (e) detecting incorporated, labeled nucleotides, thereby detecting the double-stranded DNA in the sample.

* * * * *

UNITED STATES PATENT AND TRADEMARK OFFICE
CERTIFICATE OF CORRECTION

PATENT NO. : 6,132,972
DATED : October 17, 2000
INVENTOR(S) : Y. Shigemori et al.

It is certified that error appears in the above-identified patent and that said Letters Patent is hereby corrected as shown below:

ON THE TITLE PAGE

| COLUMN | LINE | ERROR |
|---|---|---|
| [73] Pg. 1, col. 1 | Assignee | after "Ltd.," insert --Kariya-shi,-- |
| 8 (Claim 1, | 64 line 26) | "DNA in the sample, wherein" should read --DNA, wherein-- |
| 10 (Claim 2, | 3 line 16) | "protein thereby" should read --protein, thereby-- |

Signed and Sealed this

Twenty-ninth Day of May, 2001

Attest:

NICHOLAS P. GODICI

Attesting Officer    Acting Director of the United States Patent and Trademark Office